United States Patent [19]

Rothert et al.

[11] Patent Number: 4,806,477

[45] Date of Patent: Feb. 21, 1989

[54] PROCESS FOR REACTING SUBSTRATES WITH BIOCATALYSTS IN A 2-PHASE LIQUID SYSTEM

[75] Inventors: Reinhardt Rothert, Niedernhausen Taunus; Dieter Wullbrandt, Hofheim am Taunus, both of Fed. Rep. of Germany

[73] Assignee: Hoechst Aktiengesellschaft, Frankfurt am Main, Fed. Rep. of Germany

[21] Appl. No.: 55,541

[22] Filed: May 29, 1987

[30] Foreign Application Priority Data

Jun. 2, 1986 [DE] Fed. Rep. of Germany ....... 3618465

[51] Int. Cl.$^4$ .................... C12N 11/02; C12P 41/00
[52] U.S. Cl. ................................... 435/177; 435/288; 435/316; 422/140
[58] Field of Search ............... 422/140, 147, 202, 225, 422/226, 234, 146; 210/617, 618; 435/288, 299, 311, 316, 814, 177

[56] References Cited

U.S. PATENT DOCUMENTS

| | | | |
|---|---|---|---|
| 2,930,808 | 3/1960 | Zosel | 422/234 |
| 3,761,521 | 9/1973 | Alheritiere et al. | 422/225 |
| 3,901,660 | 8/1975 | Ohorodnik et al. | 422/146 |
| 4,009,099 | 2/1977 | Jeris | 210/618 |
| 4,182,675 | 1/1980 | Jeris | 210/618 |
| 4,320,089 | 3/1982 | Hüttlin | 422/140 |
| 4,397,953 | 8/1983 | Guazzone et al. | 435/216 |
| 4,589,927 | 5/1986 | Allen et al. | 422/140 |
| 4,618,418 | 10/1986 | Heijnen et al. | 422/140 |

FOREIGN PATENT DOCUMENTS

| | | | |
|---|---|---|---|
| 0011870 | 6/1980 | European Pat. Off. | 422/140 |
| 0178553 | 10/1985 | European Pat. Off. | |
| 54294 | 3/1986 | Japan | 210/617 |
| 2082164 | 3/1982 | United Kingdom | 210/617 |

OTHER PUBLICATIONS

"The Production of the Antiobiotic Patulin in a Three Phase Fluidized Bed Reactor: II. Longevity of the Biocatalyst," The Canadian Journal of Chemical Engineering, vol. 62, Feb., 1984.

*Primary Examiner*—Benoit Castel
*Attorney, Agent, or Firm*—Finnegan, Henderson, Farabow, Garrett, & Dunner

[57] ABSTRACT

A process for reacting substrates with biocatalysts in a two-phase liquid system disposed in a columnar vessel having a top portion with an exit opening and a first filter disposed therein, a bottom portion with an entrance opening and a second filter disposed therein, a feed line connecting the exit and entrance openings, and a pump disposed in the feed line. The process comprises the steps of: stirring the two-phase liquid in the columnar vessel to accelerate sedimentation and minimize accumulation of the biocatalysts in the top portion of the vessel; selectively controlling the temperature of the two-phase liquid within the vessel; drawing, with the pump, a portion of the two-phase liquid through the exit opening and first filter; and passing the drawn-off portion of the two-phase liquid through the feed line and through the entrance opening and second filter into the vessel to enhance miscibility of the individual phases of the two-phase liquid with the vessel.

1 Claim, 1 Drawing Sheet

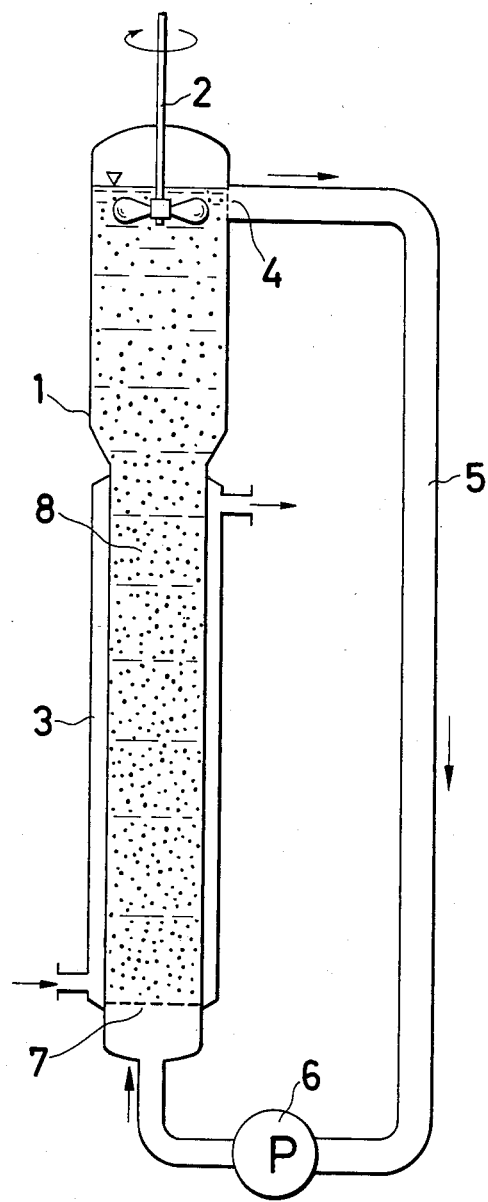

4,806,477

PROCESS FOR REACTING SUBSTRATES WITH BIOCATALYSTS IN A 2-PHASE LIQUID SYSTEM

BACKGROUND OF THE INVENTION

The fluidized-bed technique is a widely used method in chemical technology and is employed predominantly in drying processes. Fluidized-bed reactors are also encountered in fermentation technology, for example in the form of bubble columns. The antibiotic Patulin, for example, can be produced in high yields in such a reactor by means of immobilized Penicillium urticae [Berk et al., Can. J. Chem. Eng. 62, 120 (1984)].

Fluidized-bed reactors have also proven suitable in enzyme technology, in particular when immobilized enzymes are used. By means of this technology, it was possible to increase substantially the stability and hence the spacetime yield of certain enzymes, and this led therefore also to industrial application. If liquids were used in these systems, they have hitherto been composed of only one phase, predominantly aqueous solutions. In this respect, it was only possible to use such a system for substrates which are largely water-soluble.

Particularly in enzyme technology, however, it is desirable also to be able to use water-insoluble compounds as substrates. A correspondig system has hitherto been accomplished only in stirred reactors. The enzyme is then in the aqueous phase and the substrate is in an organic phase which is immiscible with water. The two phases are intimately mixed by means of stirring, so that the enzyme can reach its substrate in the form of fine droplets. This system has hitherto not been transferable to fluidized-bed reactors, because the problem of segregation of the aqueous and organic phases had not been solved. Immobolized biocatalysts can admittedly also be used in stirred reactors, but more extensive wear of the immobilized system than in the case of a fluidized-bed reactor was then observed due to increased attrition.

In order to be able to exploit the advantages of the fluidized-bed reactor also for reactions with biocatalysts in two-phase liquid systems, an appropriate device has been provided wherein, surprisingly, the feared segregation of the two liquid phases is no longer a problem.

SUMMARY OF THE INVENTION

The invention thus relates to a reactor for carrying out reactions with biocatalysts in a two-phase liquid system, which comprises a columnar vessel (1) which contains the biocatalyst and the two-phase liquid (8) and which is provided
 (a) with a stirrer (2) in the top of the vessel,
 (b) with a cooling/heating jacket (3) and
 (c) with a discharge device containing a filter screen (4) and connected
 (d) to a line (5), through which the liquid phases are recirculated into the reactor via
 (e) a pump (6) and
 (f) a feed device with a filter screen (7), the vessel and the pump being dimensioned such that the two-phase liquid mixed by the pumping energy does not segregate on passing through the vessel.

The invention also relates to a process for reacting substrates with biocatalysts in a two-phase liquid system, which comprises carrying out the reaction in a fluidized-bed reactor having a height/diameter ratio of 40:1.

BRIEF DESCRIPTION OF THE DRAWING

The FIGURE depicts a fluidized bed reactor vessel according to the present invention.

DESCRIPTION OF THE PREFERRED EMBODIMENT

The reactor (1) is of columnar shape and is expediently made of glass. Other inert materials can, however, also be used. The height/diameter ratio is preferably 40:1, and particularly preferably 20:1. The column contains the biocatalyst together with the two-phase liquid (8), i.e. the reaction takes place in the column.

The stirrer (2) in the column top prevents blocking of the discharge by any floating catalyst material and also accelerates sedimentation. For temperature control, the columnar vessel is surrounded over ½ to ⅔ of its length with a cooling or heating jacket (3). The feed device and especially the discharge device are provided with filter screens 7 and 4, respectively in order to prevent washing-out of the biocatalyst. The pore size of these screens depends on the particle diameter of the carrier and can therefore very within wide ranges. If immobilized biocatalysts are used, filter screens are employed which have a permeability of 50 to 500 $\mu$m, preferably 90 to 250 $\mu$m. All inert screen materials can be used, i.e. substances which do not significantly affect the catalyst activity. Preferably, plastic or metal screens are used. In order to ensure unhindered discharge, the corresponding discharge cross-section should appropriately be about 10% larger than the feed area.

The beed device is provided with a pump (6), by means of which the aqueous and organic phases are recirculated through the column and via a line (5), which must be made of a material which cannot be attacked by the liquid phases, into the column. Due to the pumping action, the two phases are intimately mixed with one another and the biocatalyst present in the column is fluidized. The pumping energy must be adjusted at least such that thoroughmixing of the two liquid phases in the entire column volume and hence contact between the biocatalyst and the substrate is ensured. Preferably, the reactor is run with 1.5 bed volume changes per minute. Preferably, positive displacement pumps, in particular pulsating pumps, are used.

The organic phase is immiscible or only slightly miscible with water. Given this condition, all solvents which do not adversely affect the activity of the biocatalyst are suitable.

The reactor according to the invention can advantageously be used for all reactions with biocatalysts in two-phase liquid systems. The term biocatalyst is to be understood as enzymes or cells which can be used both in the free form and in an immobilized form. if light biocatalysts are employed, the density of which is similar to that of the liquid phase used, it is advantageous to install static mixers as flow stabilizers.

The use of the reactor according to the invention is explained in more detail below by reference to examples. Percentage data relates to the weight, unless otherwise stated.

EXAMPLE 1

In the glass fluidized-bed reactor according to the invention, which has a height of 60 cm and a diameter of 2.0 cm and which, in accordance with the FIGURE, is connected by a PTFE line of 5 mm diameter to a pump via a feed and/or discharge device provided with a metal screen. By way of example and not limitation, the metal screen may be constructed of 304 or 308 alloyed steel and have a permeability of 200 m. 15 g of immobilized α-chymotrypsin prepared analogously to Example 1 of European Published application No. 0,178,553 are suspended in 430 ml of water saturated with methyl isobutyl ketone.

After a stable dispersion at a temperature of 30° C. and a circulation rate of 30 l/h have been established, the reaction is started by adding a solution of 15 g of ethyl D,L-2-(4-hydroxyphenoxy)-propionate in 20 ml of methyl isobutyl ketone.

The pH of 6.5 in the reaction solution is readjusted by adding 1-normal sodium hydroxide solution to the reaction vessel by means of an electrode and an automatic burette located in the discharge.

After about 8 hours, when 30% conversion with respect to the ester used has been reached, as determined by reference to the alkali consumption, the 2-phase reaction solution is worked up as follows:

The solution composed of ethyl L-2-(4-hydroxyphenoxy)-propionate and the remaining D-ester and the corresponding D-acid is extracted with methyl isobutyl ketone. The organic phase is dried over $NA_2SO_4$ and concentrated, and the residue is distilled in vacuo at 0.05 mm Hg at 135° C., racemized and recycled for further racemate resolution.

The aqueous phase is adjusted with hydrochloric acid to a pH of 1–2 and extracted with tertiary-butyl methyl ether The ether phase is dried over $Na_2SO_4$ and concentrated, and petroleum ether is added for crystallizing the D-2-(4-hydroxyphenoxy)-propionic acid.

An initial activity of 3 units/g was determined for the immobilized enzyme, with the racemate of ethyl 2-(4-hydroxyphenoxy)-propionate as the substrate. For determining the stability of the biocatalyst, several runs were carried out in the test apparatus described. The enzyme activities found are listed in the table which follows (Example 2).

EXAMPLE 2

8 g of ethyl D,L-2-(4-hydroxyphenoxy)-propionate dissolved in 20 ml of methyl isobutyl ketone are put into a stirred reactor provided with a pH electrode and an automatic burette, and dispersed in 240 ml of 0.1-molar phosphate buffer (pH 6.5). The reaction is started by adding 8 g of immobilized α-chymotrypsin and the pH of 6.5 is readjusted by adding 1-normal sodium hydroxide solution. 30% of the racemate has been resolved after about 24 hours.

After working up the reaction solution analogously to Example 1, the emmobilized enzyme was used repeatedly under the above conditions for the racemate resolution. The enzyme activities found are listed in the table which follows, by comparison with the values found in Example 1.

| | Units/g of carrier | |
|---|---|---|
| Batch runs | Fluidized-bed reactor (Example 1) | Stirred reactor (Example 2) |
| 1 | 2.9 | 1.5 |
| 2 | 2.9 | 1.43 |
| 3 | 2.2 | 1.49 |
| 4 | 2.9 | 1.20 |
| 5 | 2.85 | 1.27 |
| 6 | 2.8 | 1.21 |
| 7 | 3.0 | 1.01 |
| 8 | 3.0 | 1.20 |
| 9 | 3.2 | 0.91 |
| 10 | 3.2 | 1.12 |

The optical purity of the D-2-(4-hydroxyphenoxy)-propionic acid obtained from Examples 1 and 2 was determined to be 95% of enantiomer excess: $[\alpha]_D^{20}+42.3°$ (c=1 in ethanol).

No decrease in enzyme selectivity in the course of time was observable.

EXAMPLE 3

The procedure followed is as in Example 1, but a dispersion of 1,000 ml of water and 60 g of ethyl D,L-2-(4-hydroxyphenoxy)-propionate dissolved in 80 ml of methyl isobutyl ketone is fed in continuously at a rate of 45 ml/h, in such a way that a conversion of 30% is established in the system. It was possible to operate this continuous procedure over a period of 200 hours without a noticeable decrease in enzyme activity.

We claim:
1. A process for reacting substrates with biocatalysts in a 2-phase liquid system disposed in a fluidized bed reactor vessel having a height to diameter ratio of between 40:1 to 20:1, a top portion with an exit opening and first filter means disposed therein, a bottom portion with an entrance opening and second filter means disposed therein, a feed line connecting the exit and entrance openings, and pump means disposed in the feed line, comprising the steps of:
   stirring the 2-phase liquid in the vessel with a stirrer disposed in the top portion thereof to accelerate sedimentation and minimize accumulation of the biocatalysts in the top portion of the vessel;
   selectively controlling the temperature of the 2-phase liquid within the vessel with a cooling/heating jacket surrounding a portion of the vessel;
   drawing, with the pump means, a portion of the 2-phase liquid through the exit opening and first filter means; and
   recirculating the drawn-off portion of the 2-phase liquid through the feed line and through the entrance opening and second filter means to enhance miscibility of the individual phases of the 2-phase liquid within the vessel.

* * * * *